(12) United States Patent
Abi-Jaoudeh et al.

(10) Patent No.: US 10,743,773 B2
(45) Date of Patent: Aug. 18, 2020

(54) IMAGING THERMOMETRY

(71) Applicant: KONINKLIJKE PHILIPS N.V., Eindhoven (NL)

(72) Inventors: Nadine Abi-Jaoudeh, Washington, DC (US); Ming Li, Potomac, MD (US); Samuel Kadoury, Olney, MD (US); Ankur Kapoor, Cranbury, MD (US); Nicolaas Jan Noordhoek, Best (NL); Alessandro Guido Radaelli, Oirschot (NL); Bart Carelsen, Eindhoven (NL); Bradford Johns Wood, Bethesda, MD (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1624 days.

(21) Appl. No.: 14/396,064

(22) PCT Filed: Apr. 26, 2013

(86) PCT No.: PCT/IB2013/053329
§ 371 (c)(1),
(2) Date: Oct. 22, 2014

(87) PCT Pub. No.: WO2013/164746
PCT Pub. Date: Nov. 7, 2013

(65) Prior Publication Data
US 2015/0150466 A1      Jun. 4, 2015

Related U.S. Application Data

(60) Provisional application No. 61/641,315, filed on May 2, 2012.

(51) Int. Cl.
*A61B 6/03*      (2006.01)
*A61B 6/00*      (2006.01)
(Continued)

(52) U.S. Cl.
CPC .......... *A61B 5/015* (2013.01); *A61B 5/0035* (2013.01); *A61B 5/4839* (2013.01);
(Continued)

(58) Field of Classification Search
CPC ..... A61B 5/015; A61B 5/0035; A61B 5/4839; A61B 5/7278; A61B 6/12; A61B 6/032;
(Continued)

(56) References Cited

U.S. PATENT DOCUMENTS 6,377,834 B1    4/2002    Zhou et al.
6,684,097 B1    1/2004    Parel et al.
(Continued)

FOREIGN PATENT DOCUMENTS

| CN | 101390748 A | 3/2009 | |
|---|---|---|---|
| CN | 202821311 U | 3/2013 | |
| WO | WO-2008009656 A1 * | 1/2008 | ............... G06T 7/20 |

OTHER PUBLICATIONS

Bentzen, S. M., et al.; Isotherm mapping in hyperthermia using subtraction X-ray computed tomography; 1984; Radiotherapy and Oncology; 2:255-260.
(Continued)

*Primary Examiner* — Boniface N Nganga
(74) *Attorney, Agent, or Firm* — Larry Liberchuk

(57) ABSTRACT

A computing device includes a thermal map generator (142) that generates a thermal map for image data voxels or pixels representing a volume or region of interest of a subject based on thermometry image data, which includes voxels or pixels indicating a change in a temperature in the volume or region of interest, and a predetermined change in value to temperature lookup table (144) and a display (145) that visually presents the thermal map in connection with image data of the volume of interest. A method includes generating a thermal map for image data voxels or pixels representing a
(Continued)

volume or region of interest of a subject based on thermometry image data, which includes voxels or pixels indicating a change in a temperature in the volume or region of interest, and a predetermined change in voxel or pixel value to temperature lookup table.

25 Claims, 3 Drawing Sheets

(51) Int. Cl.

| | |
|---|---|
| A61B 5/00 | (2006.01) |
| A61B 5/01 | (2006.01) |
| A61B 6/12 | (2006.01) |
| A61B 34/20 | (2016.01) |
| G06T 7/30 | (2017.01) |
| A61B 18/14 | (2006.01) |
| A61B 18/18 | (2006.01) |
| A61B 18/20 | (2006.01) |
| A61N 7/02 | (2006.01) |
| A61B 18/00 | (2006.01) |
| A61B 17/00 | (2006.01) |
| A61B 90/00 | (2016.01) |
| A61B 34/10 | (2016.01) |

(52) U.S. Cl.
CPC ............ *A61B 5/7278* (2013.01); *A61B 6/032* (2013.01); *A61B 6/12* (2013.01); *A61B 6/4417* (2013.01); *A61B 6/4441* (2013.01); *A61B 6/463* (2013.01); *A61B 6/466* (2013.01); *A61B 6/5247* (2013.01); *A61B 6/5264* (2013.01); *A61B 18/1477* (2013.01); *A61B 18/1815* (2013.01); *A61B 18/20* (2013.01); *A61B 34/20* (2016.02); *A61N 7/02* (2013.01); *G06T 7/30* (2017.01); *A61B 6/4085* (2013.01); *A61B 6/487* (2013.01); *A61B 2017/00084* (2013.01); *A61B 2018/00577* (2013.01); *A61B 2018/00791* (2013.01); *A61B 2018/00982* (2013.01); *A61B 2018/1425* (2013.01); *A61B 2018/1869* (2013.01); *A61B 2018/2005* (2013.01); *A61B 2018/205547* (2017.05); *A61B 2034/107* (2016.02); *A61B 2090/376* (2016.02); *A61B 2090/3762* (2016.02); *A61B 2090/3764* (2016.02); *A61N 7/022* (2013.01); *A61N 2007/025* (2013.01); *G06T 2207/10081* (2013.01); *G06T 2207/30024* (2013.01)

(58) Field of Classification Search
CPC ..... A61B 6/4085; A61B 6/4417; A61B 6/441; A61B 6/463; A61B 6/466; A61B 6/487; A61B 6/5247; A61B 6/5264; A61B 18/1477; A61B 18/1815; A61B 18/20; A61B 2018/00577; A61B 2018/00791; A61B 2018/00982; A61B 2018/1425; A61B 2018/1869; A61B 2018/2005; A61B 2018/205547; A61B 2090/376; A61B 2090/3762; A61B 2090/3764; A61N 7/02; A61N 2007/025; G06T 7/30; G06T 2207/10081; G06T 2207/30024

See application file for complete search history.

(56) References Cited

U.S. PATENT DOCUMENTS

| | | | |
|---|---|---|---|
| 7,078,903 B2 | 7/2006 | Paliwal | |
| 7,787,663 B2 | 8/2010 | Hartlove | |
| 7,871,406 B2 | 1/2011 | Nields et al. | |
| 8,279,997 B2 | 10/2012 | Shechter | |
| 8,519,711 B2 | 8/2013 | Sakakura | |
| 8,636,980 B2 | 1/2014 | Elgort | |
| 8,867,811 B2 | 10/2014 | Raju | |
| 9,399,148 B2 | 7/2016 | Anand | |
| 9,971,003 B2 | 5/2018 | Kohler | |
| 2006/0258927 A1* | 11/2006 | Edgar, Jr. ........... | A61B 5/14551 600/336 |
| 2008/0033418 A1 | 2/2008 | Nields et al. | |
| 2008/0100612 A1* | 5/2008 | Dastmalchi ............ | A61B 3/102 345/418 |
| 2008/0111881 A1* | 5/2008 | Gibbs .................. | H04N 5/2259 348/36 |
| 2010/0080350 A1 | 4/2010 | Kalender et al. | |
| 2010/0088041 A1* | 4/2010 | Ringermacher ....... | G01N 25/72 702/40 |
| 2010/0284598 A1 | 11/2010 | Zhao | |
| 2011/0046472 A1 | 2/2011 | Schmidt et al. | |
| 2014/0100452 A1* | 4/2014 | Jain ..................... | A61B 8/0841 600/424 |

OTHER PUBLICATIONS

Braak, S. J., et al.; Real-time 3D Flouroscopy Guidance During Needle Interventions: Technique, Accuracy, and Feasibility; 2010; American Journal of Roentgenology; 194(5)W445-W451.

Brace, C. L., et al.; Periodic contrast-enhanced computed tomography for thermal ablation monitoring: A feasibility study; 2009; IEEE EMBS; pp. 4299-4302.

Brace, C. L., et al.; Thermal Ablation for the Treatment of Abdominal Tumors; 2011; Journal of Visualized Experiments; pp. 1-5.

Bruners, P., et al.; CT-based temperature monitoring during hepatic RF ablation: Feasibility in an animal model; 2012; Int. J. Hyperthermia; 28(1)55-61.

Chang, C-C., et al.; Modified temporal difference method for change detection; 2005; Optical Engineering; 44(2)027001-14.

Cho, Y. K., et al.; Radiofrequency ablation versus surgical resection as primary treatment of hepatocellular carcinoma meeting the Milan criteria: A systematic review; 2011; Journal of Gastroenterology and Hepatology; 26:1354-1360.

Durucan, E., et al.; 2001; Proc. of the IEEE; 89(10)1368-1380.

Glocker, B., et al.; Dense image registration through MRFs and efficient linear programming; 2008; Medical Image Analysis; 12:731-741.

Griffiths, H., et al.; Applied potential tomography for non-invasive temperature mapping in hyperthermia; 1987; Clin. Phys. Physiol. Meas.; vol. 8, Suppl. A:147-153.

Jenne, J. W., et al.; CT On-Line Monitoring of HIFU Therapy; 1997; IEEE Ultrasonics Symposium; vol. 2:1377-1380.

Jin, C., et al.; High-intensity focused ultrasound combined with transarterial chemoembolization for unresectable hepatocellular carcinoma: Long-term follow-up and clinical analysis; 2011; European Journal of Radiology; 80:662-669.

Kim, J-E., et al.; Outcomes of patients with hepatocellular carcinoma referred for percutaneous radiofrequency ablation at a tertiary center: Analysis focused on the feasibility with the use of ultrasonography guidance; 2011; European Journal of Radiology; 79:e80-e84.

Komodakis, N., et al.; Performance vs computational efficiency for optimizing single and dynamic MRFs: Setting the state of the art with primal-dual strategies; 2008; Computer Vision and Image Understanding; 112:14-29.

Lencioni, R., et al.; Image-guided thermal ablation of hepatocellular carcinoma; 2008; Critical Reviews in Oncology/Hematology; 66:200-207.

Li, M., et al.; Towards cone-beam CT thermometry; 2013; Proc. of SPIE; vol. 8671; pp. 86711I-1-7.

Munk, P. L., et al.; Cone-Beam Computed Tomography as an Adjunct to Performance of Percutaneous Cementoplasty of the Acetabulum; 2012; Can. Assoc. Radial. J.; 63 (3 Suppl.) S7-S10.

Radke, R. J., et al.; Image Change Detection Algorithms: A Systematic Survey; 2005; IEEE Trans. on Image Processing; 14(3)299-307.

(56) References Cited

OTHER PUBLICATIONS

Rivera, M. J., et al.; Analytical Validation of COMSOL Multiphysics for Theoretical Models of Radiofrequency Including the Hyperbolic Bioheat Transfer Equation; 2010; IEEE EMBS; 3214-3217.
Solomon, S. B., et al.; Imaging in Interventional Oncology; 2010; Radiology; 257(3)624-640.
Suprijanto, S., et al.; Inter-frame Motion Correction for MR Thermometry; 2005; MICCAI-LNCS; 3749:580-588.
Wlodarczyk, W., et al.; Three-Dimensional Monitoring of Small Temperature Changes for Therapeutic Hyperthermia Using MR; 1998; J. Mag. Res. Imaging; 8(1)165-174.
Wyatt, C., et al.; Hyperthermia MR Temperature Measurement: Evaluation of Measurement Stabilization for Extremity and Breast Tumors: 2009; Int. J. Hyperthermia; 25(6)422-433.

\* cited by examiner

IMAGING THERMOMETRY

CROSS REFERENCE TO RELATED APPLICATIONS

This application is a national filing, of PCT application Serial No. PCT/IB2013/053329, filed Apr. 26, 2013, published as WO 2013/164746 A1 on Nov. 7, 2013, which claims the benefit of U.S. provisional application Ser. No. 61/641,315 filed May 2, 2012, which is incorporated herein by reference.

STATEMENT REGARDING FEDERALY SPONSORED RESEARCH OR DEVELOPMENT

The United States Government has certain rights to this invention pursuant to NIH CRADA No. 01864.

The following generally relates to imaging thermometry and is described with particular application to computed tomography (CT) in connection with an interventional procedure in which temperature monitoring of tissue being treated is of interest. The following is also amenable to other imaging such as x-ray, fluoroscopy and/or other imaging used in connection with such interventional procedures.

A limitation of some interventional procedures like ablation is a high recurrence rate due to under-ablation or inadequate safety margin. Furthermore, some complications are caused by over-ablation, which may damage adjacent healthy tissue. Real-time temperature monitoring may facilitate mitigating such issues and allow for iterative interventional procedure plan adjustment for preventing under-ablation, overtreatment and/potential damage to adjacent tissue.

Magnetic resonance (MR) imaging can be used to monitor temperature changes in tissue during ablation and/or other procedures. With MR imaging, a change in temperature causes a linearly proportional change in the resonant frequency of protons within a magnetic field, and is thus temperature change is detectable using a phase sensitive pulse sequence scanning called "proton resonant frequency shift (PRFS)." With PRFS, two images are obtained at two different points in time and the phase difference between them is used to calculate the temperature difference at each pixel. PRFS imaging results in temperature sampling densities of volume equal to densities of the image pixels. This data is used for planning and delivery and post-treatment assessment of tissue damage.

However, ablations are typically performed with ultrasound or CT guidance; rarely is MR guidance used during ablations because of limited MR compatible equipment and/or MR scanners access. Unfortunately, real-time temperature monitoring currently is not possible with CT, and predetermined ablation zones provided by manufacturers do not take into account tissue properties, heterogeneity of tumor tissue, heat sync, or patient motion. Many factors affect the ablation zone including patient characteristics, tumor histology and location, and the type of energy used for the ablation. Moreover, computational models can be time consuming and rely on heavy mathematical calculations.

Aspects described herein address the above-referenced problems and others.

In one aspect, a computing device includes a thermal map generator that generates a thermal map for image data voxels or pixels representing a volume or region of interest of a subject based on thermometry image data, which includes voxels or pixels indicating a change in a temperature in the volume or region of interest, and a predetermined change in voxel or pixel value to temperature lookup table and a display that visually presents the thermal map in connection with image data of the volume or region of interest.

In another aspect, a method includes generating a thermal map for image data voxels or pixels representing a volume or region of interest of a subject based on thermometry image data, which includes voxels or pixels indicating a change in a temperature in the volume or region of interest, and a predetermined change in voxel or pixel value to temperature lookup table.

In another aspect, a computer readable storage medium is encoded with computer readable instructions. The computer readable instructions, when executed by a processor, cause the processor to: generate and display a thermal map for image data voxels or pixels representing a volume or region of interest of a subject during an interventional procedure based on thermometry image data, which includes voxels or pixels indicating a change in a temperature in the volume or region of interest, and a predetermined change in voxel or pixel value to temperature lookup table.

The invention may take form in various components and arrangements of components, and in various steps and arrangements of steps. The drawings are only for purposes of illustrating the preferred embodiments and are not to be construed as limiting the invention.

FIG. 1 schematically illustrates an example imaging system in connection with a computing device configured for real-time temperature monitoring of tissue of interest for interventional procedures using image data.

The following describes an approach for generating and presenting a thermal map for a volume or region of interest in an object or subject for a needle based interventional procedure, such as RF, laser, microwave, HIFU, etc. ablation and/or pharmaceutical delivery, based on baseline and intermittent CT data, such as cone beam CT and/or conventional CT data, and/or x-ray or fluoroscopy data. Generally, the thermal map is generated and presented in real-time (i.e., as the ablation or pharmaceutical delivery is being performed), which allows the interventionalist to mitigate under-ablation (and hence subsequent ablation to finish the ablation), over-ablation, and ensure adequate safety margins. Furthermore, it mitigates risk of infection and/or bleeding related to insertion of thermocouples to measure temperature in the volume or region of interest. Moreover, the approach compensates for patient motion (e.g., due to breathing, etc.) and the low resolution image data.

Figure 1:
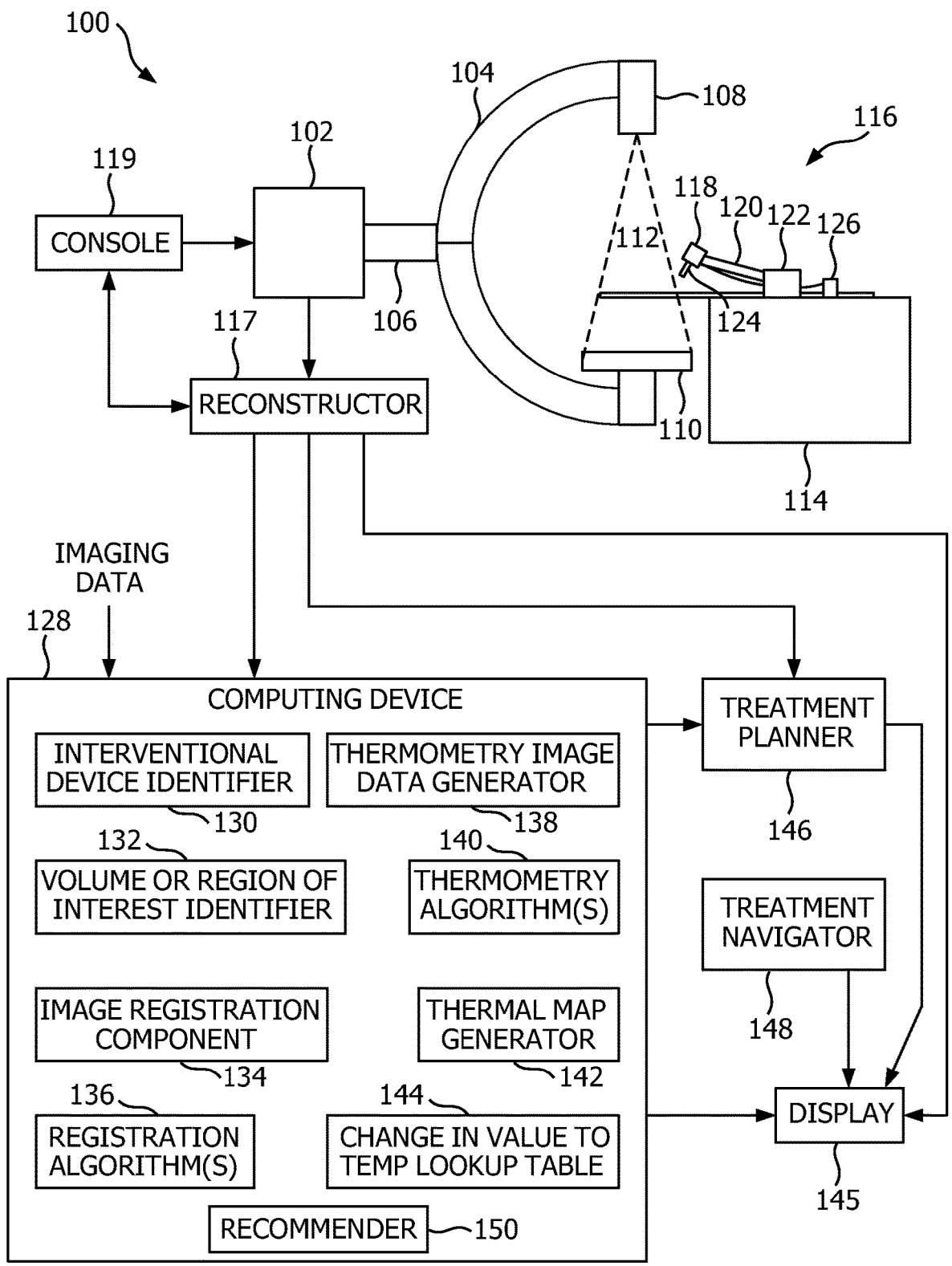

FIG. 1 schematically illustrates an imaging system 100. For sake of brevity and clarity, the following discusses the approach in connection with a C-arm CT scanner. However, the imaging system 100 can alternatively be a convention CT scanner or x-ray imager. The scanner includes stationary portion 102, which can be mounted to a ceiling, wall, floor, generally stationary device in an examination room, a portable device with wheels or the like which can be readily transported into and out of the examination room, etc. A C-arm 104 is pivotably coupled to the stationary portion 102 via a coupling 106 and is configured to pivot through a predetermined arc (e.g., at least 180 degrees). The C-arm 104 can be pivoted before, during and/or after a scanning.

A radiation source 108 is coupled to one end of the C-arm 104, and a radiation sensitive detector array 110 is coupled to the other end of the C-arm 104. The radiation source 108 is separated from the detector array 110 forming an examination region 112 there between. A suitable detector array 110 includes a two-dimensional (2D) detector array such as a flat panel detector or the like. The detector array 110 generates a signal in response to detecting radiation. At least one of source 108 or the detector 110 may also move independent of the C-arm 104, for example, towards one another and/or displaced within a sleeve along the C-arm 104. The radiation source 108/detector array 110 can be used to acquire cone beam CT, fluoroscopy, and/or other image data.

A subject support 114 supports a subject in the examination region 112. A reconstructor 117 reconstructs the signal output by the detector array 110 and generates volumetric image data. A console 119 controls the imaging system 100, including pivoting the C-arm 104 to a particular angular orientation with respect to the examination region 112, activating the source 108 to emit radiation, activating the detector array 110 to detect radiation, and receiving and/or conveying information with another device.

An interventional device holder 116 includes a device support 118 for holding an interventional device, an arm 120 for positioning the device support 118 and hence an interventional device supported thereby, and a base 122 that removably affixes to the subject support 114 and supports the arm 120. The arm 120 may be moveable through manual and/or electronic means. An interventional device 124 such as an ablation device is shown supported by the device support 118. An interventional device controller 126 controls the interventional device 124, for example, turning the device on and off. In the illustrated embodiment, the interventional device controller 126 includes hand activated controls, such as a joy stick or the like, that affix to the subject support 114 and control the interventional device 124. In another instance, a foot activated control such as a foot pedal or the like can be used to control the interventional device 124.

A computing apparatus or device 128 processes imaging data, such as imaging data generated by the imaging system 100 and/or one or more other imaging systems. The image data includes baseline image data, for example, image data from a scan after needle placement or after needle replacement to another position and before the needle is used for an interventional procedure to confirm needle position. The image data also includes intermittent image data, for example, image data from one or more scans acquired at one or more different time points during the needle based interventional procedure, for example, to monitor progress of the needle based interventional procedure, such as the temperature of the tissue being treated and surrounding tissue. From the baseline and intermittent image data, the computing apparatus 128 generates a thermal map for a predetermined volume or region of interest. As described in greater detail below, the thermal map allows for real-time temperature monitoring while compensating for motion and indicates heat distribution of tissue being treated without using specialized devices such as thermocouples, which may lengthen the procedure, increase the risk of complications (e.g., due to additional needles), and only provide a single point temperature.

A treatment planner 146 allows an intervention list to plan and/or modify an interventional procedure plan based on the baseline, intermittent, thermal map, and/or other information. By way of non-limiting example, the baseline image data and the temperature map can be used by the intervention list to ensure proper needle placement, complete ablation, and mitigation of damage to healthy tissue. For example, from this data, the intervention list can decide whether the needle placement is appropriate or needs to be moved, whether to continue or stop the ablation based on the temperature of the tissue being treated and/or surrounding tissue, etc. A treatment navigator 148 visually presents image data that guides the intervention list with inserting and placing the interventional needle with respect to the tissue to be treated.

In the illustrated embodiment, the computing apparatus 128 includes an optional recommender 150. The recommender 150, in one instance, provides guidance back to the user regarding on the generated thermal map via the display 145, audio, and/or otherwise. In one non-limiting instance, the guidance demonstrates where additional heat is needed and optionally provides a path that will ensure the thermal dose is delivered satisfactorily. In another non-limiting instance, the guidance, if a thermal procedure plan is satisfied, provides data that can be used for updating the plan in "real-time," thereby tracking the progress of the treatment.

In the illustrated embodiment, the computing apparatus 128 includes an interventional device identifier 130, a volume or region of interest identifier 132, an image registration component 134 and registration algorithm(s) 136, a thermometry image generator 138 and difference algorithm(s) 140, and a thermal map generator 142 and a change in value to temperature lookup table 144. The computing apparatus 128 includes at least one processor that executes at least one computer readable instruction stored in computer readable storage medium, such as physical memory or other non-transitory storage medium to implement one or more of the components 130, 132, 134, 138, or 142. The processor may also execute one or more computer readable instructions carried by a carrier wave, a signal or other transitory medium.

The interventional device identifier 130 identifies, in the example, the interventional device needle tip in the baseline image data and in the intermittent image data. In one instance, the interventional device identifier 130 identifies the tip using an automatic object of interest identifying algorithm. In another instance, the interventional device identifier 130 identifies the tip based on user input, for example, identification of the tip using a user identified tip perimeter, a user positioned and size adjusted predetermined geometrical shape, etc. Results of automatic, semi-automatic and manual approaches are confirmed and can be changed by an authorized user.

The volume or region of interest identifier 132 identifies a volume or region of interest about the identified ablation needle tip (or an ablation zone) in the baseline image data and in the intermittent image data. In one instance, the volume or region of interest identifier 132 identifies the volume or region of interest using an automatic region of interest algorithm, for example, based on a predetermined margin outside the identified tip region. In another instance, the region of interest identifier 132 identifies the region based on user input, for example, a user identified region outside the identified tip region. Pre-determined manufacturer zones can also be used to facilitate identifying the volume or region of interest. Results of automatic, semi-automatic and manual approaches are confirmed and can be changed by an authorized user.

The image registration component 134 registers the baseline and intermittent image data based on one or more of the registration algorithms 136, including rigid and/or elastic (non-rigid) registration algorithms. An example of a suitable registration algorithm is a deformable image registration that compensates for motion between the baseline and intermittent acquisitions such as breathing and/or other motion. The following discusses a non-limiting example of such an algorithm.

Given a baseline image $I_1$ and an intermittent image $I_2$, defined on a domain $\Omega$ ($\Omega \in R^3$ in the case of volume registration), the images are related as shown in EQUATION 1:

$$(x) = h \cdot I_1(Tx), \qquad \text{EQUATION 1}$$

for all x on $\Omega$, involving a geometric B-spline deformation T and a non-linearity h explaining the changes of appearance between corresponding points. The deformation T can be estimated on a sparse grid $\Omega' \subset \Omega$ ($|\Omega'| \ll |\Omega|$) of control points, as shown in EQUATION 2:

$$Tx = x + \Sigma_{p \in \Omega'} \rho(\|x - x_p\|) \Delta_p, \qquad \text{EQUATION 2}$$

where $\Delta_p$ is the displacement vector of the control point $x_p$. Moving a control point results in a local deformation of the image around it; the weighting function $\rho$ measures the contribution of a control point in $\Omega'$ to the displacement of a point in $\Omega$.

The deformation field is found by minimizing the criterion of point-wise similarity between the target and deformed source images, as shown in EQUATION 3:

$$E_{data}(T) = \frac{1}{|\Omega'|} \sum_{p \in \Omega'} \int_\Omega \rho^{-1}(\|x - x_p\|) d(I_2(x), I_1(Tx)) dx, \qquad \text{EQUATION 3}$$

where d is some similarity function. In order to avoid folding on the deformation grid, a smoothness term on T is added, rendering EQUATION 4:

$$E_{smooth}(T) = \frac{1}{|\Omega'|} \sum_{p \in \Omega'} \phi(|\nabla_\Omega d_p|), \qquad \text{EQUATION 4}$$

For one solution, EQUATION 3 can be posed as an assignment problem in the following way[9]: Let $L = \{u^1, \ldots, u^k\}$ be a discrete set of labels corresponding to a quantized version of the deformation space $\Theta = \{\Delta^1, \ldots, \Delta^k\}$. A label assignment $u_p \in L$ to a grid node $x_p \in \Omega'$ is associated with displacing the node by the corresponding vector $\Delta^{u_p}$.

The deformation field associated with a certain discrete labeling $u: \Omega' \to L$ is $T_u x = x + \Sigma_{p \in \Omega'} \rho(\|x - x_p\|) \Delta^{u_p}$. EQUATION 3 can thus be posed as discrete Markov random field (MRF) optimization with respect to the labeling, as shown in EQUATION 5:

$$E_{smooth}(T) = \frac{1}{|\Omega'|} E_{total}(u)$$

$$= \frac{1}{|\Omega'|} \sum_{p \in \Omega'} \int_\Omega \rho^{-1}(\|x - x_p\|) d(I_2(x), I_1(T_u x))$$

$$dx + \frac{1}{|\Omega'|} \sum_{p \in \Omega'} \phi(|\nabla_\Omega d_p|)$$

$$\approx \frac{1}{|\Omega'|} \sum_{p \in \Omega'} V_p(u_p) + \frac{1}{|\Omega'|} \sum_{p \in \Omega'} \sum_{q \in N(p)} V_{pq}(u_p, u_q), \qquad \text{EQUATION 5}$$

where $V_p$ is a singleton potential function representing a local dissimilarity measure, while $V_{pq}$ are the pairwise potential functions. For optimizing the resulting MRF, an optimal label is assigned to each node so that the MRF energy in EQUATION 5 is minimized. To this end, a discrete optimization technique that builds upon principles drawn from the duality theory of linear programming can be used to efficiently derive almost optimal solutions for a very wide class of NP-hard MRFs.

Again, the above registration example is provided for explanatory purposes and is not limiting; other registration algorithms are also contemplated herein.

The thermometry image generator 138 generates thermometry image data from the registered baseline and intermittent image data based on one or more of the thermometry algorithms 140. An example of a suitable thermometry algorithm 140 is a Wronskian change detector, which detects a difference between the baseline and intermittent image data, where a temperature difference is a component of the overall difference between the image data. An example of a Wronskian change detector that detects changes in low signal to noise ratio image data is discussed in Durucan et al., "Change detection and background extraction by linear algebra," Proceedings of the IEEE. 89, 1368-1381, 2001.

Generally, the Wronskian change detector is based on: 1) vector model of images, and 2) concepts of linear dependence/independence between vectors. By modeling the image as an ensemble of vectors, changes in their lengths or directions (with respect to the initial unchanged status) can be exploited. Mathematically, this corresponds to the concepts of linear dependence and linear independence, respectively. The decision as to whether a vector is linearly dependent on another provides the possibility to decide whether there has been a change or not. One test for determining the linear dependence or independence of vectors is the Wronskian determinant.

By way of example, consider a region of support also referred as block defined about a center pixel. The number of pixels, w, on either side of this center pixel is defined as the half width of the block. The window width of the region of support is 2w+1. The vectorization of a 3×3 image block (w=1), denoted by vec(I), can be represented as shown in EQUATION 6:

$$I = \begin{bmatrix} x_{11} & x_{12} & x_{13} \\ x_{21} & x_{22} & x_{23} \\ x_{31} & x_{32} & x_{33} \end{bmatrix} \qquad \text{EQUATION 6}$$

$$vec(I) = [x_{11}, x_{12}, x_{13}, x_{21}, x_{22}, x_{23}, x_{31}, x_{32}, x_{33}].$$

The use of a vector of a block in image allows us to make a decision as to whether there is a change based on the possibility that the vector is linearly dependent on another or not. The above definition of vectorization of EQUATION 6 can be extended to 3D data. For example, a 3×3×3 image block w=1 can be vectorized as shown in EQUATION 7:

$$I_k = \begin{bmatrix} x_{11k} & x_{12k} & x_{13k} \\ x_{21k} & x_{22k} & x_{23k} \\ x_{31k} & x_{32k} & x_{33k} \end{bmatrix} \qquad \text{EQUATION 7}$$

$$vec(I) = [\, vec(I_1) \quad vec(I_2) \quad vec(I_3) \,],$$

where $I_k \, \forall k \in [-1, 1]$ is the $k^{th}$ slice in the 3D image series.

A Wronskian model for detecting changes between two images (modeled as two vectors $I_1$ and $I_2$) is shown in EQUATION 8:

$$W = \frac{1}{n}\left(\sum_{i=1}^{n} \frac{x_i^2}{y_i^2} - \sum_{i=1}^{n} \frac{x_i}{y_i}\right), \quad \text{EQUATION 8}$$

where $x_i$ and $y_i$ are corresponding components in the vectors I and J, respectively. n is the size of the region of support. If $W \neq 0$, then changes occur in the position of pixel i, otherwise there is no change. In fact, W computes the negative of the sum of the first derivative of the function $$f \equiv \frac{x_i}{y_i}.$$

The value would increase as the ratio of components increases. Change to this value would be due to contribution of a block of pixels rather than any individual pixel alone.

Again, the above approach to generating thermometry image data is provided for explanatory purposes and is not limiting, and other approaches such as a sum of squared differences for example are also contemplated herein.

The thermal map generator 142 generates a pixel-wise or voxel-wise thermal or temperature map (e.g., a stack of 2D images centered on the volume of interest) for a region or volume of interest based on the thermometry image and the change in value to temperature lookup table 144, which provides a mapping between the thermometry image data and temperature. To generate the change in value to temperature lookup table 144, a uniform phantom such as an agar gel, water, anatomical, and/or other phantom is scanned at a reference temperature (e.g., room temperature or 37° C.) and one or more other predetermined or known higher temperatures (e.g., 42° C. to 82° C.).

A least-squares, Chi-square, and/or other approach can be used to fit a linear, cubic, etc. model to the mean value of the thermometry image and the temperatures such that $\Sigma_{i-1}{}^n \|y_i - y(x_i; p_1, \ldots, p_m)\|^2$, where m=2 or 4. The result can be minimized for the best fit, where n is number of data points and $p_i$ are the parameters of the model. The number of parameters m for linear and cubic models are 2 and 4, respectively. The inverse of the calibration is stored as the lookup table 144.

Figure 2:
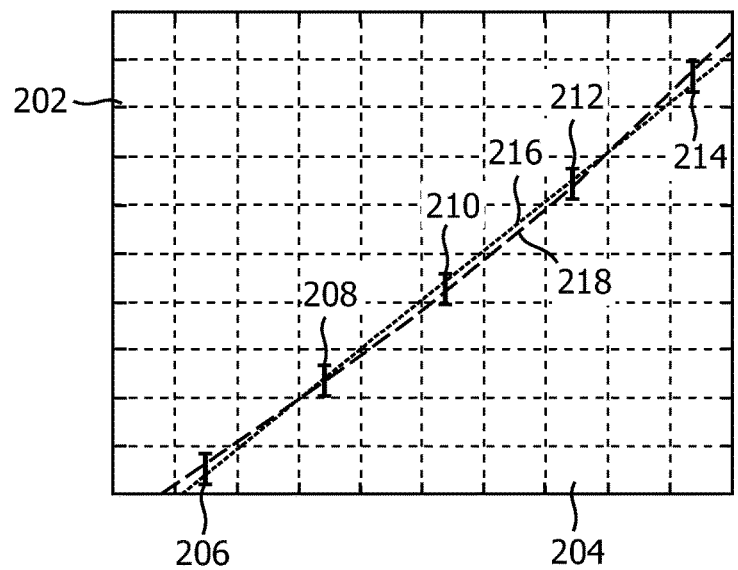
FIG. 2 illustrates a relationship between a change in voxel or pixel value and temperature of the tissue the voxel or pixel represents.

FIG. 2 shows an example change in value to temperature lookup table 144. In FIG. 2, a y-axis 202 represents the mean value of the thermometry image value and an x-axis 204 represents temperature. In this example, curves are generated based on five (5) data 206, 208, 210, 212 and 214 acquired at five (5) different temperatures. A first curve 216 corresponds to a linear fit to the data 206-214, and a second curve 218 corresponds to a cubic fit to the data 206-214. The curves 216 or 218 can be saved as the lookup table 144, a polynomial, and/or otherwise.

Figure 3:
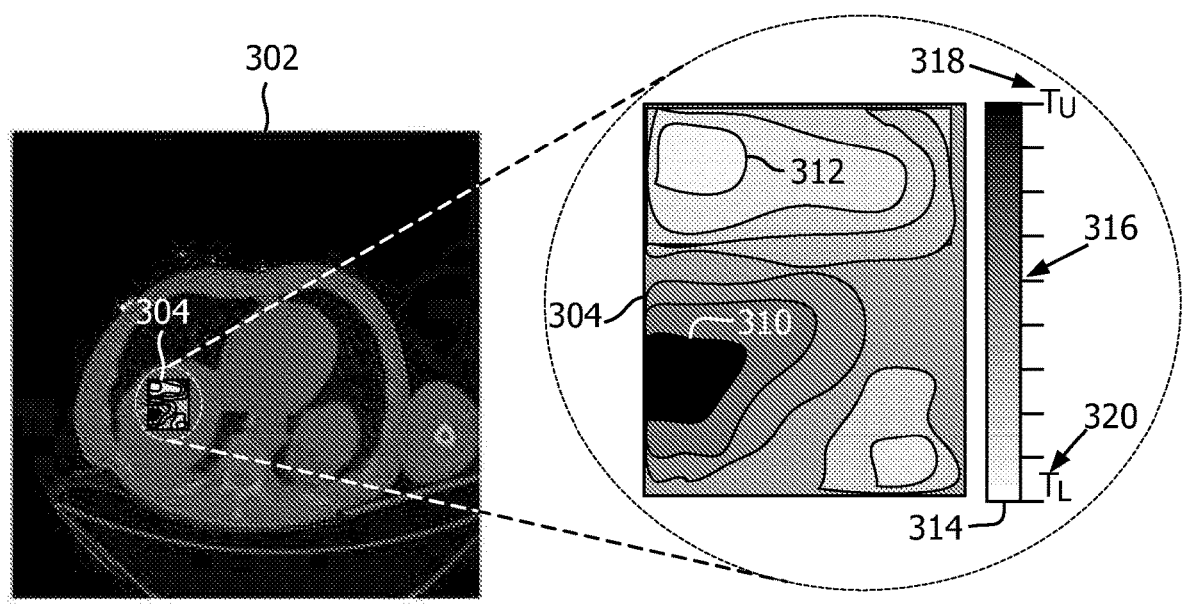
FIG. 3 illustrates a baseline image with a temperature map superimposed over a volume or region of interest.

The computing apparatus 128 presents the baseline image and the temperature map via a display 145. An example of this is shown in connection with FIG. 3, which shows a 2D baseline image 302 or a 2D baseline image 302 from the volume image data with a 2D temperature map or map portion 304 (of a 3D temperature map) corresponding thereto superimposed over the identified needle tip. One axis 306 of the temperature map portion 304 represents pixels or voxels along one direction, and the other axis 308 of the temperature map portion 304 represents pixels or voxels along another direction, such that the temperature map portion 304 represents a 2D array of pixels or voxels of the region or volume of interest.

In this example, a gray-scale is used to represent temperature, with white representing a baseline temperature of the region or volume of interest before heating, black representing a pre-determined maximum temperature of interest, and levels of gray there between transitioning from lighter to darker with an increase in temperature. In a variation, white can be used to represent the pre-determined maximum temperature of interest and black can be used to represent the baseline temperature of the region or volume of interest before heating. In another variation, color can be used instead of the gray scale.

In the illustrated example, a first region 310 around the needle tip is hotter than a second region 312 farther away from the needle tip, and this is visually shown through the different shades of gray. An optional graphical key 314 can be visually presented mapping gray level to temperature value using tics 316 corresponding particular temperatures and/or corresponding to predetermined temperature increments between particular upper and lower temperatures $T_U$ 318 and $T_L$ 320, and/or other approaches.

A 3D volume (the entire volume or a sub-portion thereof) can additionally or alternatively be displayed in a 3D volume rendered, with the 3D temperature map (the entire map or a sub-portion thereof) superimposed over the volume of interest about the identified needle tip. Optionally, the 3D temperature map can be superimposed to the predetermined treatment plan displaying the desired ablated 3D zones. Additionally or alternatively, one or more 2D slices, for example, in an axial, sagittal, coronal, curved, oblique, etc. planes and displayed along with a corresponding portion of the 3D temperature map.

Optionally, one or more of the intermittent image data, the thermometry image data, and/or other data is also displayed, in addition to or in alternative to the baseline image and the temperature map.

Figure 4:
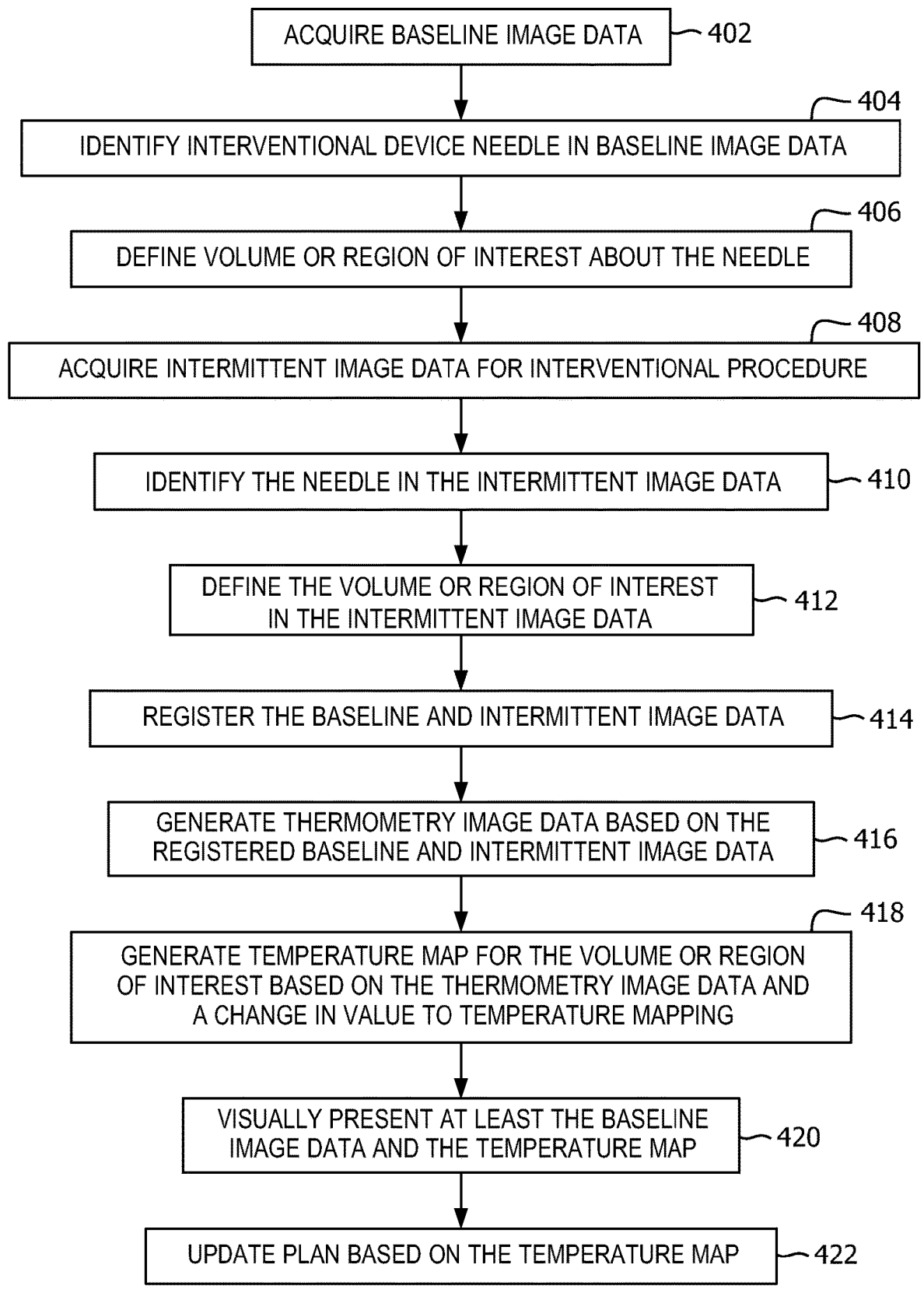
FIG. 4 illustrates an example method for monitoring tissue temperature during an interventional procedure.

FIG. 4 illustrates a non-limiting method.

It is to be appreciated that the ordering of the acts in the methods described herein is not limiting. As such, other orderings are contemplated herein. In addition, one or more acts may be omitted and/or one or more additional acts may be included.

At 402, a baseline scan is performed, generating baseline image data. As discussed herein, for an ablation procedure, the scan may correspond to a scan after initial or subsequent re-placement of an interventional device needle with respect to tissue to be treated.

At 404, the interventional device needle is identified in the baseline image data.

At 406, a volume or region of interest about the interventional device needle is defined in the baseline image.

At 408, during the interventional procedure, an intermittent scan is performed, generating intermittent image data.

At 410, the interventional device needle is identified in the intermittent image data.

At 412, the volume or region of interest is also defined about the interventional device needle in the intermittent image data.

At 414, the baseline and intermittent image data are registered. As discussed herein, a suitable registration algorithm includes a deformable registration that compensates for subject motion.

At 416, thermometry image data is generated based on the registered baseline and intermittent image data. As discussed herein, a suitable algorithm includes the Wronskian change detector algorithm.

At 418, a temperature map for the volume or region of interest is generated based on the thermometry image data and a mapping between change in voxel or pixel value and temperature.

At 420, at least the baseline image and the temperature map are visually presented through a display monitor. Optionally, one or more of the intermittent image data, the thermometry image data, and/or other data is also displayed, in addition to or in alternative to the baseline image and the temperature map.

At 422, optionally, the temperature map is used to adjust the interventional procedure plan.

At least a portion of the above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An imaging system configured to monitor a temperature of a volume or region of interest, comprising:
at least one processor configured to:
generate thermometry image data based on baseline computed tomography image data and subsequently acquired intermittent computed tomography image data, wherein the thermometry image data includes voxels or pixels indicating a change in the temperature in the volume or region of interest, wherein the volume or region of interest is heated between the acquisition of the baseline and the acquisition of the intermittent computed tomography image data, and wherein the thermometry image generator employs a Wronskian change detector algorithm to generate the thermometry image data;
generate a thermal map for image data voxels or pixels representing the volume or region of interest based on the thermometry image data, and a predetermined change in voxel or pixel value to temperature lookup table; and
a display configured to visually present the thermal map in connection with the image data of the volume or region of interest.

2. The imaging system according to claim 1, wherein the change in temperature corresponds to heating from an interventional procedure, and the visually presented thermal map indicates whether the interventional procedure is complete.

3. The imaging system according to claim 2, wherein the visually presented thermal map indicates whether an interventional procedure margin is adequate.

4. The imaging system according to claim 1, wherein the at least one processor is further configured to employ the Wronskian change detector algorithm to detect a temperature difference between the baseline computed tomography image data and the subsequently acquired intermittent computed tomography image data.

5. The imaging system according to claim 1, wherein the baseline image data and the intermittent image data include low resolution image data, and the at least one processor is configured to process the low resolution image data with the Wronskian change detector algorithm to generate the thermometry image data.

6. The imaging system according to claim 4, wherein the Wronskian change detector algorithm includes a vector model of images and an indication of at least one of a linear dependence or independence between vectors, and the at least one processor is further configured to model the image data as an ensemble of vectors, changes in vector lengths or vector directions.

7. The imaging system according to claim 1, wherein the at least one processor is further configured to receive and register
the baseline image data and the intermittent image data, such that the thermometry image data is based on the registered image data.

8. The imaging system according to claim 7, wherein the at least one processor is further configured to employ a deformable registration algorithm to register the baseline image data and the intermittent image data.

9. The imaging system according to claim 8, wherein the deformable registration algorithm compensates for motion of the volume or region interest of interest between acquisitions for obtaining the baseline and intermittent image data.

10. The imaging system according to claim 1, wherein the volume or region of interest includes a safety margin.

11. The imaging system according to claim 1, wherein the thermal map is displayed using a predetermined gray scale which indicates a relative temperature difference between different regions of the volume or region of interest.

12. The imaging system according to claim 11, wherein the thermal map includes a key which maps a gray level to a corresponding temperature value.

13. The imaging system according to claim 1, wherein the thermal map is displayed using a predetermined color map which indicates a relative temperature difference between different regions of the volume or region of interest.

14. The imaging system according to claim 13, wherein the thermal map includes a key which maps a color to a corresponding temperature value.

15. An imaging method for monitoring a temperature of a volume or region of interest, comprising:
generating thermometry image data based on baseline computed tomography image data and subsequently acquired intermittent computed tomography image data, wherein the thermometry image data includes voxels or pixels indicating a change in the temperature in the volume or region of interest, wherein the volume or region of interest is heated between the acquisition of the baseline and the acquisition of the intermittent computed tomography image data, and a Wronskian change detector algorithm generates the thermometry image data; and
generating a thermal map for image data voxels or pixels representing the volume or region of interest based on the thermometry image data and a predetermined change in voxel or pixel value to temperature lookup table.

16. The method according to claim 15, further comprising:

visually presenting the thermal map in connection with image data of the volume or region of interest.

17. The method according to claim 16, wherein the thermal map is displayed using a predetermined gray scale or color mapping which indicates a relative temperature difference between different regions of the volume or region of interest.

18. The method according to claim 17, further comprising:
visually presenting a key along with the thermal map, wherein the key maps a gray level or color to a corresponding temperature value.

19. The method according to claim 15, further comprising:
employing the thermal map to adjust an interventional procedure plan for treating tissue of the volume or region of interest.

20. The method according to claim 19, wherein the adjustment includes at least one of continuing the interventional procedure or terminating the interventional procedure.

21. The method according to claim 15, further comprising:
employing the Wronskian change detector algorithm to detect a temperature difference between the baseline computed tomography image data and the subsequently acquired intermittent computed tomography image data.

22. The method according to claim 21, further comprising:
modeling the image data as an ensemble of vectors, changes in vector lengths or vector directions, wherein the Wronskian change detector algorithm includes a vector model of images and an indication of at least one of a linear dependence or independence between vectors.

23. The method according to claim 15, further comprising:
registering the baseline image data and the intermittent image data; and
generating the thermometry image data based on registered image data.

24. The method according to claim 23, wherein a deformable registration algorithm compensates for motion of the volume or region of interest to register the baseline image data and the intermittent image data.

25. A non-transitory computer-readable medium having one or more executable instructions stored thereon which, when executed by at least one processor, cause the at least one processor to perform an imaging method for monitoring a temperature of a volume or region of interest, the method comprising:
generating thermometry image data based on baseline computed tomography image data and subsequently acquired intermittent computed tomography image data, wherein the thermometry image data includes voxels or pixels indicating a change in a temperature in the volume or region of interest, wherein the volume or region of interest is heated between the acquisition of the baseline and the acquisition of the intermittent computed tomography image data, and wherein a Wronskian change detector algorithm generates the thermometry image data; and
generating and displaying a thermal map for image data voxels or pixels representing the volume or region of interest during an interventional procedure based on the thermometry image data and a predetermined change in voxel or pixel value to temperature lookup table.

* * * * *